(12) United States Patent
Faucher et al.

(10) Patent No.: US 8,264,221 B2
(45) Date of Patent: Sep. 11, 2012

(54) EDDY CURRENT PROBE ASSEMBLY ADJUSTABLE FOR INSPECTING TEST OBJECTS OF DIFFERENT SIZES

(75) Inventors: Denis Faucher, Québec (CA); Benoit Lepage, Québec (CA)

(73) Assignee: Olympus NDT, Waltham, MA (US)

( * ) Notice: Subject to any disclaimer, the term of this patent is extended or adjusted under 35 U.S.C. 154(b) by 532 days.

(21) Appl. No.: 12/533,417

(22) Filed: Jul. 31, 2009

(65) Prior Publication Data

US 2011/0025316 A1  Feb. 3, 2011

(51) Int. Cl.
- *G01N 27/82* (2006.01)
- *G01N 27/72* (2006.01)
- *G01R 11/02* (2006.01)
- *G01R 33/00* (2006.01)

(52) U.S. Cl. .................. 324/240; 324/137; 324/227

(58) Field of Classification Search .............. 324/240
See application file for complete search history.

(56) References Cited

U.S. PATENT DOCUMENTS

| | | |
|---|---|---|
| 2,882,488 A | 6/1954 | Price et al. |
| 3,612,987 A | 10/1971 | Placke et al. |
| 4,101,832 A | 7/1978 | Baker et al. |
| 4,641,092 A | 2/1987 | Sakamoto et al. |
| 4,785,243 A | 11/1988 | Abramczyk et al. |
| 5,111,142 A | 5/1992 | Mazzone et al. |
| 5,412,319 A | 5/1995 | Ciani |
| 5,517,114 A * | 5/1996 | Reitz et al. ............ 324/262 |
| 5,638,000 A | 6/1997 | Förster |
| 7,242,186 B2 * | 7/2007 | Zimmermann ............ 324/242 |
| 7,888,932 B2 * | 2/2011 | McKnight et al. ......... 324/242 |
| 2007/0222438 A1 | 9/2007 | Reeves |

FOREIGN PATENT DOCUMENTS

| | | |
|---|---|---|
| DE | 4121948 A1 | 7/1993 |
| DE | 43 24 332 A1 | 1/1995 |
| GB | 2 014 317 A | 8/1979 |
| GB | 2 034 049 A | 5/1980 |
| GB | 2 277 994 A | 11/1994 |
| WO | WO 86/04413 | 7/1986 |

OTHER PUBLICATIONS

*Advanced Manual for: Eddy Current Test Method*, Canadian General Standards Board, National Standard of Canada, CAN/CGSB-48.14-M86, Reaffirmed May 1997, pp. 59-60.
Search Report issued by European Patent Office in connection with corresponding application No. EP 10 17 1040 on Nov. 3, 2010.

* cited by examiner

*Primary Examiner* — Roberto Velez
(74) *Attorney, Agent, or Firm* — Ostrolenk Faber LLP

(57) ABSTRACT

An eddy current probe assembly suitable for inspecting a test object with longitudinal shape, being passed through the assembly in the object's axial direction during an inspection session, the probe assembly comprising multiple probe modules being disposed in a radial plane and with the modules partially overlaying on each other forming an iris structure encircling an inspection zone, wherein a movement in unison of each of the probe modules closer to or further away from the center of the inspection zone makes the inspection zone enlarged or contracted. Spring tension is applied on each of the probe modules so that constant life-off in maintained between the probe modules and the test surface. Array of eddy current elements for each probe module and multiple layers of probe modules can be employed to achieve complete coverage of the test surface. The radial cross-sectional shapes of the test objects can be of round or polygonal.

18 Claims, 7 Drawing Sheets

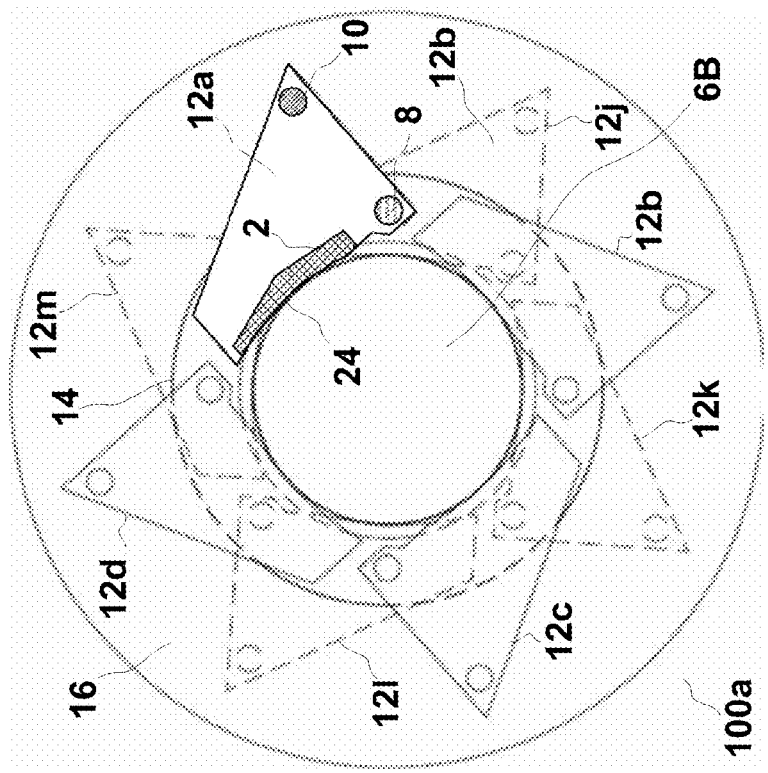
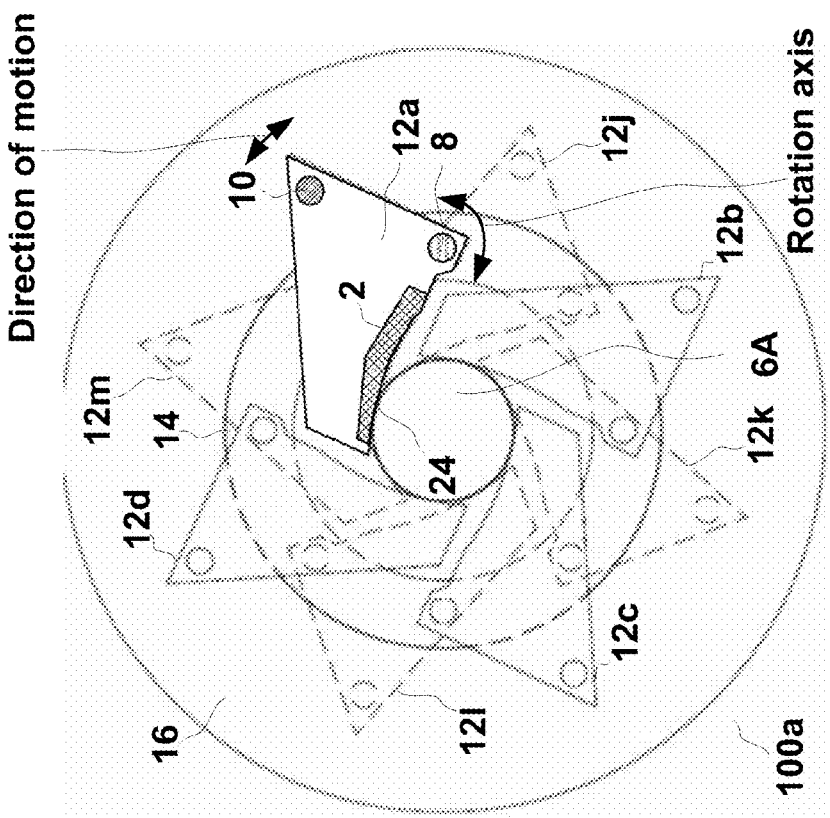
FIG. 1A
FIG. 1B

EDDY CURRENT PROBE ASSEMBLY ADJUSTABLE FOR INSPECTING TEST OBJECTS OF DIFFERENT SIZES

FIELD OF THE DISCLOSURE

The present disclosure generally relates to a method and system for non-destructive testing and inspection (NDT/NDI) of test objects, more specifically, to a method and system which provide an inspection probe assembly that can be adjusted easily for inspecting test objects of different sizes.

BACKGROUND OF THE DISCLOSURE

Presently, testing for defects for quality control on test objects such as wire, rods or tubes is frequently performed by using eddy current (EC) technologies. The testing often involves having the test objects travel along a work path, passing through eddy current probe(s).

The technical issues associated with conventional eddy current NDT/NDI systems include a) maximizing test coverage of test object surfaces, b) accommodating test objects of different sizes by means of efficient probe adjustment, and c) maintaining a uniform distance between the sensing surface of the probes and the test object surface (i.e. the lift-off distance).

Drawbacks associated with these systems are as follows.

U.S. Pat. Nos. 3,919,628 and 4,641,092 present a well practiced inspection technique that employs a single eddy current probe affixed to a rotating head that typically provides coverage helicoidally around a test object at high rotational speeds. This "rotating head" technique is characterized by a high rotation speed and a relatively complicated mechanical design that requires considerable maintenance. The helical gap between rotations typically limits the longitudinal resolution making the detection of very small longitudinal defects troublesome. Furthermore, it is not feasible to inspect test objects that are not round shaped with this technique.

An alternate inspection technique employs one or multiple eddy current coils (elements) with each coil completely encircling the test object. The size and shape of the "encircling coils" must substantially match the size and shape of the test object due to the critical lift-off requirement for the coils. Various attempts have been made to overcome this limitation, such as those presented in U.S. Pat. No. 5,412,319 and U.S. Pat. No. 5,638,000. However, various disadvantages involving the encircling coil technique remain. The most notable of these is the dependency of detection sensitivity on the circumference of the object being inspected resulting in significantly limited detectability of circumferential defects. Consequently, it is not possible to localize the circumferential position of defects. Also, with this type of arrangement, although it is possible to detect large defects, substantially smaller defects remain undetected because of the signal averaging process used in this type of system.

To overcome the limitations associated with encircling coils and the rotating head technique, an alternate EC inspection technique employs many smaller coils that are aligned in an array surrounding the outer surface of a test object being moved through the inspection zone of the EC array. U.S. Pat. No. 4,785,243 describes an example of this technique. Using this method, surface coverage and detectability are improved compared to encircling coils and rotating head techniques. However, these techniques require a probe that exactly matches the size and shape of the test object in order to limit the lift-off because many eddy current elements are disposed in a rigid fixture. One unique probe, which is relatively expensive, must be used for each test object size and shape. In addition, operation cost associated with changing the probes to accommodate various test objects is quite high.

Another solution to facilitate insertion of the test object into the inspection zone and to accommodate for slight variations of test object size involves the use of multiple small coils affixed to multiple probe heads. The surface of the probe heads onto which the eddy current elements are affixed is shaped to match the surface of the test object. These probe heads can be brought into proximity of the surface of the test object by various means. U.S. Pat. No. 4,101,832 describes one such approach for which a plurality of eddy current receiver coils are mounted on and supported by a plurality of probe heads that surround the part, each of the four probe heads covering a respective quadrant of the circumference of the test object. Although some flexibility in accepting test object with variable sizes is provided, this flexibility is very limited, particularity for small diameter test object.

Other inspection systems provide a somewhat limited means of lift-off compensation. These systems provide gain versus test object diameter graphs for each element for a given calibration diameter, typically fixed. As these gain versus test object diameter graphs are provided at the factory, changing the diameter of the calibration test object in the field is problematic and leads to relatively extensive recertification to obtain relevant gain versus inspection test object diameter graphs for the new diameter.

It would therefore be beneficial to provide an eddy current probe assembly that is easier and more efficient for the inspection of one test object size to another while maintaining high test resolution and high inspection productivity. It is therefore more economical to build such an EC system with fewer kinds EC probe heads and less down-time associated with changing probe heads.

SUMMARY OF THE DISCLOSURE

The invention disclosed herein solves the aforementioned drawbacks related to probes, sensors and assemblies of such for NDT/NDI devices. More particularly, exemplary embodiments of this disclosure solve the problems related to eddy current probes of single or multiple coils, the assembly of such used in eddy current inspection systems.

Accordingly, it is a general object of the present disclosure to provide a method and system which provide eddy current (EC) inspection probes that can be adjusted easily for inspecting test objects with variable sizes wherein the test objects have elongated shapes such as a bar or tube and are passed through the inspection probes axially.

It is further an object of the present invention to provide an EC probe head wherein multiple probe modules are formed in a partially overlaying iris fashion, with each probe module being able to rotate independently closer to or further from the center of the iris, therefore forming an inspection zone that can be enlarged or contracted.

Test objects can be loaded and passed through the inspection zone axially. The multiple probe modules are disposed in such a fashion to encircle the passing test objects.

It is further an object of the present invention to provide an EC probe assembly to achieve complete circumferential coverage of the test object by using 1) multiple eddy current elements (coils) forming one probe module; 2) partially overlaying multiple probe modules forming a probe head encircling the inspection zone, and 3) several probe heads disposed along the test object axially, wherein the probe modules of one probe head are off-set circumferentially from the probe modules of the adjacent probe heads.

It is further an object of the present invention to provide an EC probe head to achieve constant circumferential proximity to the outer surface of the test object among all probe modules by using the same kind of probe module assembly and the same rotating and spring force means applied on each probe module so that the probe modules all lean against the test object with substantially equal force applied to the test object.

It is further an object of the present invention to provide an EC probe head to achieve constant proximity to the outer surface of a round test object by constructing curvature at the surface of the probe module leaning against the test object, wherein the diameter of the curvature is made to fit the outer surface of the largest test object that the probe head is designed to inspect.

It is further an object of the present invention to provide a set of guide wheels on both ends of a group of probe heads to hold and transport the test object to pass through the center of the inspection zone, wherein the center of the iris (or the center of the inspection zone) is aligned with the axial center of the test objects.

It is further an object of the present invention to provide a set of guide wheels for each probe head to hold and transport the test object to pass through the center of the inspection zone, wherein the center of the iris (or the center of the inspection zone) is aligned with the axial center of the test objects and the guide wheels are attached to the supporting structure of the respective probe module.

It is further an object of the present invention to provide a method and system which can achieve all of the above described objectives for test objects having elongated shapes, such as a bar or a column, with polygonal or round perimeter cross-section shape. Furthermore, the inspection system can accommodate different sizes of the test objects without the need to change probe heads or the probe assembly between respective test object sessions.

Adaptability to many test object sizes for a given test object shape is provided by the presently disclosed invention without the need to change any probe components. Multiple and partially overlapping probe modules shaped and sized to fit the test objects as well as multiple probe heads radially off-set and complementarily covering the full circumference of the test object are all advantageously designed to provide complete and high resolution inspection coverage for a range of test object sizes, with minimum operation cost.

In all embodiments subsequently described, the advantages of the invention related to improved inspection coverage and resolution are best exploited using a plurality of eddy current coils, preferably disposed in multiple rows or in a fashion of an array.

Note that the terms "probe", "transducer", and "sensor" used herein may be used interchangeably.

Also note that "EC assembly" denotes to the presently invented assembly including probe modules, probe heads and other supporting and guiding/transporting means configured according to present disclosure. The "EC inspection system" in the subsequent detailed disclosure denotes to a conventional EC inspection system with presently invented EC assembly installed.

BRIEF DESCRIPTION OF THE DRAWINGS

FIG. 1A and FIG. 1B are cross-sectional views showing a preferred embodiment of the present disclosure wherein the invented ECA probe assembly is configured to inspect two stocks cylindrical bars of smaller diameter and larger diameter, respectively.

DETAILED DESCRIPTION OF PREFERRED EMBODIMENTS OF THE PRESENT DISCLOSURE

Figure 2:
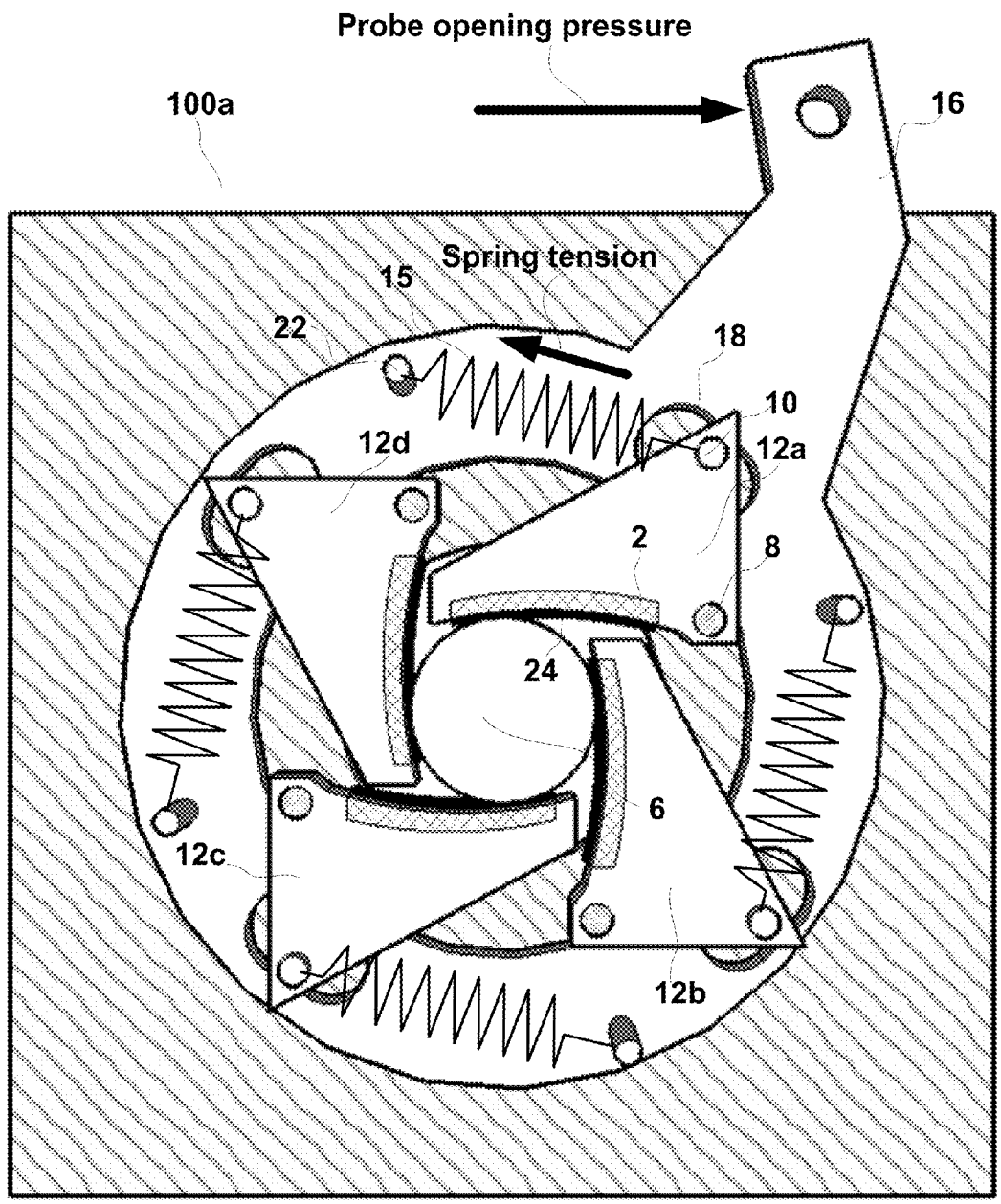
FIG. 2 is a cross-sectional view of a probe head of the preferred embodiment of the present invention.

It should be noted that the subject titles used in this and subsequent detailed descriptions are purposed to make the descriptions more organized and easier to be followed. However, the scope of any content of this description should not be construed with any restriction from the subject titles herein used.

The 'Iris' Structure and Adjustable Size of the Inspection Zone

Referring to FIG. 1A and FIG. 1B, a probe head 100a is shown in this preferred embodiment designed for testing round test objects with different diameters, such as round bars 6A and 6B. Probe head 100a is comprised of probe modules 12a to 12d surrounding a space (an inspection zone) wherein round bars 6A and 6B are disposed. Probe modules 12a to 12d are grouped into an axial plane. Similarly probe modules 12j to 12m are included in another probe head 100b (later shown in FIG. 3) and grouped into another axial plane surrounding the inspection zone.

Note that the terms 'round bars (or test object)', 'probe modules' and 'probe heads' are collectively referred to herein as 6, 12 and 100 respectively.

An EC assembly herein disclosed comprises guide wheels 36 (later shown in FIG. 3) to hold and transport round bars 6A and 6B passing through the inspection zone surrounded by probe heads, such as 100a and 10b.

Referring to exemplary probe module 12a of FIG. 1, each probe module 12 includes an eddy current array (ECA) 2 which contains many eddy current elements. At least a portion of ECA 2 is in close proximity with the outer surface of round test object 6. Each probe module 12 is attached to backing support 14 by a rotation pivot pin 8. Each probe module includes a diameter adjustment pin 10. Force exerted on adjustment pin 10 induces a rotation of probe module 12 around rotation pivot pin 8. In the direction of motion, a clockwise force exerted on diameter adjustment pin 10 forces probe module 12a and its associated eddy current array 2 to move away from the surface of test object 6. Conversely, a counterclockwise force exerted on diameter adjustment pin 10 forces probe module 12a to move towards the center of the inspection zone thereby forcing the eddy current array 2 onto to the outer surface of test object 6.

Simultaneous forces on all adjustment pins 8 for all probe modules 12 can induce either a contraction of the inspection zone, with counter-clockwise force, or a dilation of the inspection zone, with a clockwise force. This mechanism can therefore be advantageously employed for consecutively loading test objects of different sizes and diameters due to the ability of the EC system to easily adapt in concert with the inline test object loading process.

Probe head 100a with multiple EC probe modules 12 surrounding the expandable and contractible inspection zone is referred to herein as an 'Iris'.

Test Object Holding and Transporting Means

Referring now to FIG. 2, which shows a cross-section view of probe head 100a comprising four probe modules 12a to 12d. Note that less than four or more than four probe modules can be used in the same group without deviating from the scope of the invention As shown in FIG. 2, and FIG. 1a and FIG. 1b, exemplary probe module 12a is rotatable around rotation pivot pin 8 which also serves as an attaching means to backing support 14.

Referring now to FIG. 2, diameter adjustment pin 10 is attached to rotation support plate 16 via a spring 15 which is fastened to pin 10 and pin 22 to provide spring tension on diameter adjustment pin 10 in a counterclockwise direction. Furthermore, the range of rotation of probe module 12a is limited by means of a groove or slot opening 18 in rotation support plate 16 in which diameter adjustment pin 10 is restrained. Applying an opening pressure to rotation support plate 16 in a clockwise direction provides clockwise force on diameter adjustment pin 10 wherein pin 10 abuts to the edge of the slot opening 18. Applying probe opening pressure to rotation support plate 16 provides simultaneous opening control on all four probe modules 12a to 12d.

As can be seen, the forces acting on the adjustment pins 10 to contract the iris can be from sources of independent springs or alternative methods. The spring-like forces will keep each probe module 12 in contact with test object 6 despite slight variations in the position of test object 6 with respect to the central axis of the inspection zone, thereby maintaining a uniform lift-off between eddy current array elements 2 and test object 6.

Test object 6 is longitudinally fed through the inspection zone. Right before the leading end of object 6 reaches probe head 100, probe opening pressure is applied to rotation support plate 16 to release probe modules 12 and keep them in the open position. As soon as the leading end of test object 6 is positioned at the start of the inspection zone, probe opening pressure is released resulting in the application of spring tension at to adjustment pin 10. This in turn forces probe module 12 to close around test object 6, typically until contact is made between wear plate 24 of probe module 12a and the test object 6. At this point, the EC inspection is started for the newly loaded object 6. Substantially uniform spring tension means is provided for probe modules 12a to 12d, acting simultaneously on every probe module 12 associated to probe head 100a. Spring tension provides substantially uniform pressure on probe modules 12 in order to maintain modules 12 in contact with test object 6 at all times during the inspection.

The process of opening and closing the iris is repeated for each test object being moved into probe head 100.

Figure 3:
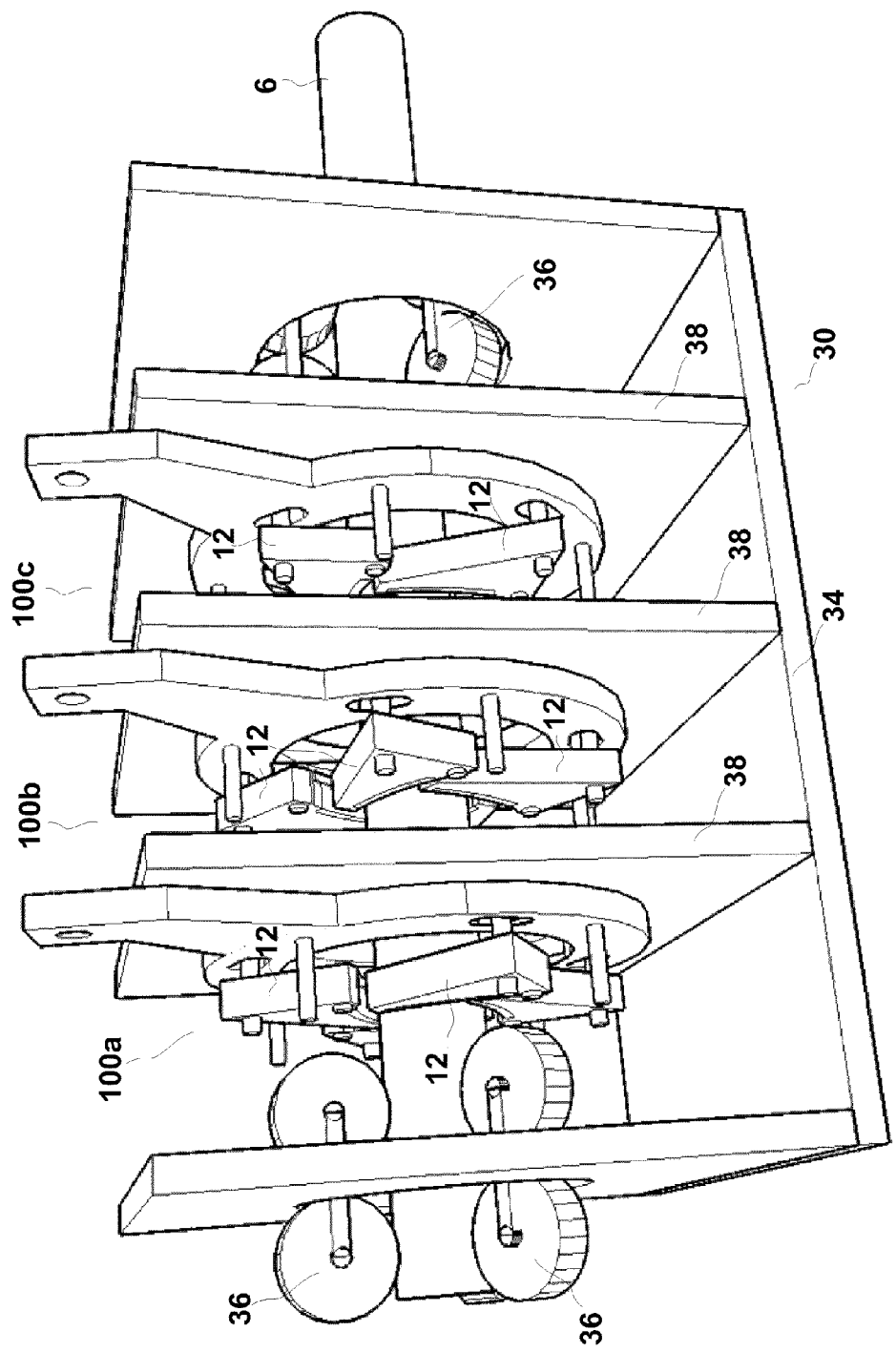
FIG. 3 is an isometric view showing an eddy current probe assembly of multiple probe heads in the preferred embodiment of the present invention.

The inspection zone must be readily and repeatedly opened and closed to allow insertion and inspection of test objects. This process is repeated at high speeds for consecutive test objects. The loading, moving, and centering of test object 6 in this preferred embodiment is achieved by using a group of guide wheels 36 as shown in FIG. 3. As used in some existing EC systems, the guide wheels are configured to move and center test objects of different sizes.

It should be recognized that alternative means are possible to transport and inspect test objects without deviating from the scope of the invention. A few other conventionally practiced designs can be adopted by and combined with the present disclosure to achieve variable inspection requirements. For example, as opposed to providing contact between the probe modules and the test object using spring tension, the "closed" inspection positions of the probe modules can be fixed at positions by a probe module stopper (not shown), so that the probe modules can come to very close to but not in contact with the test objects, as it is deployed by other existing EC system. The position of probe module stopper is adjusted according to the size of the test object. Note that compensation for variability in the position of the test object is not as readily achieved with this fixed position approach. Also note that typical wire and rod inspection systems using a centering device both prior to and following EC probe(s) can also be adopted and combined with the presently invented probe assembly to maintain consistency of the positioning of the test object with respect to the probe modules.

Complete Eddy Current Coverage

A single eddy current coil provides very limited coverage for defect detection. A typical coil will provide an effective coverage of about half of its coil diameter. Therefore, in order to provide adequate coverage over the full circumference of the test object 6, multiple coils in an array overlapping each other are installed in each probe module 12.

Referring back to FIG. 1A and FIG. 1B, another aspect of present disclosure seeking complete EC coverage of test object involves shaping the inspection surface 24 of the eddy current array 2 on each probe module 12 to advantageously maximize the proximity between array 2 and the surface of test object 6 for a given range of test object diameters. With this novel design, different elements of the array will be in very close proximity to the surface of test object 6 depending on the diameter of the test object. In the preferred embodiment, the diameter of curvature of inspection surface 24 is slightly greater than the diameter of the largest test object 6B. For large test objects, such as 6B, a significant portion of elements of each eddy current array 2 will be in proximity with the surface of test object 6B. For smaller diameter test objects, such as 6A, a lesser portion of elements of the eddy current array 2 will be in proximity to the surface of the test object.

As can be noticed in FIGS. 1A and 1B, the novel iris-like, overlapping design of multiple modules also serves to maximize complete EC coverage object 6.

Continuing with FIG. 1A and 1B, due to limited space available on a probe head, additional groups of probe modules are used and aligned in an offset manner in multiple radial parallel planes in the longitudinal direction of test object 6 in order to maximize test coverage. For example, probe modules 12a through 12d are grouped in one plane as probe head 100a. Probe modules 12j through 12m are offset longitudinally from 100a and in another radial plane.

Turning now to FIG. 3, to ensure complete and precise surface coverage for the entire circumference of test objects, multiple probe heads described above are installed into an EC assembly 30. As can be seen, multiple groups of probe modules are disposed back-to-back longitudinally. Each the group of probe modules is referred to as probe heads 100a, 100b and 100c. In order to improve circumferential inspection coverage, probe modules 12 of each probe head 100 is preferably offset from its adjacent ones at an angle so that they cover complementary sections of the surface of test object 6. In this manner, each section of the arc of the circumferential surface of the round test object 6 is at least covered sufficiently by the inspecting range of the eddy current array of module 12.

Factors affecting the number of probe modules needed include the range of diameters of round test objects and the inspection precision required. The overall quantity of probe modules is defined by the diameter range of test objects that need to be inspected and the maximum allowable lift-off variation.

Continuing with FIG. 3, ECA assembly 30 includes guide wheels 36 for guiding and moving test object 6 though the inspection zone surrounded by probe modules 12.

Probe heads 100 as shown in FIG. 3 are attached to support 34 by solid but not permanent attaching means, which is commonly used with guide wheels 36. Two sets guide wheels 36 are used in the preferred embodiment at the leading and trailing ends of the EC assembly 30 respectively. The means for attaching the probes heads to support 34 is preferably via vertical supports 38. It must be recognized that up to two probe heads can be attached to a single vertical support 38 in order to reduce the overall axial length of the inspection system.

The assembly of guide wheels 36 and inspection heads 100 are solidly affixed together. However, existing practice can be adopted to provide a certain amount of mobility in relation to the test object feeding and transportation to compensate for slight variability in the position of test object 6 as it is fed through system 30. Springs or other mechanical type suspension as well as resilient material could be used at the base of structure of 30 to provide a degree of mobility to the assembly of probe heads 100 and guide wheels 36. This allows slight variations in positioning of the object as the object is fed through the inspection system by some type of feeding system. Guide wheels 36 provide a means to maintain constant positioning of test object 6 with respect to the probe modules 12 of inspection system 30. This type of loading and centering mechanism is well known to those skilled in the art and can be well combined with the novel probe heads as disclosed herein.

Lift-Off Compensation

In eddy current technology, lift-off is defined as the distance between the eddy current element and the surface of the test object. Maintaining constant lift-off has significant effects on the accuracy of eddy current inspection. Notably, the smaller the lift-off, the stronger the signal from a given indication or defect. For this reason, the preferred embodiment of the invention described herein employs a method in combination with the above described novel EC assembly for compensating lift-off variations among many elements in each eddy current array.

Figure 4:
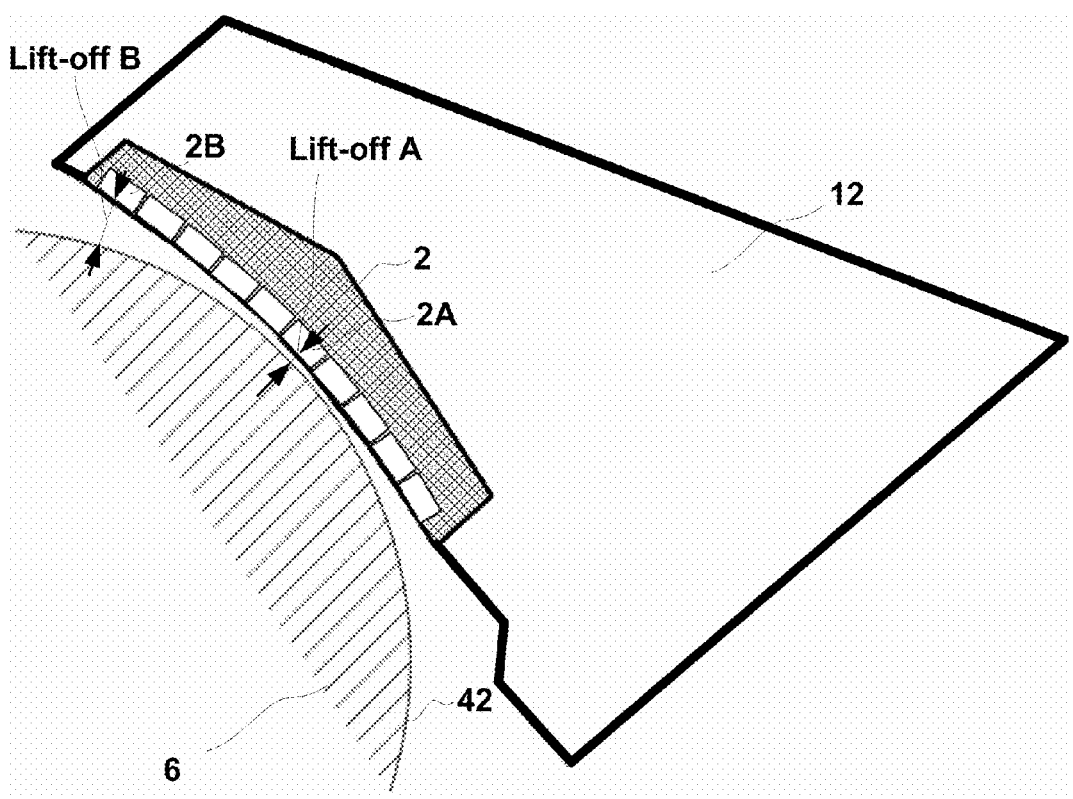
FIG. 4 is a zoomed-in cross-section view of a single probe module of the presently disclosed ECA probe assembly.

Referring now to FIG. 4 in connection with FIGS. 1-3, FIG. 4 shows a zoomed-in and more detailed view of probe module 12, its EC array 2 and round test object 6. Array 2 contains a plurality of eddy current elements, including elements 2A and 2B. The kind of the eddy current elements can be one of or any combination of pancake coils, pancake coils with ferrite cores, PCB etched eddy current coils, cross-wound coils, etc. Usage of other coil types can be recognized by one skilled in the art and remains within the scope of the current invention. The invention described herein allows for overlapping of eddy current elements combined with a mechanism that provides limited and controlled lift-off for a range of diameters of test object, notably covering relatively small diameter test objects.

For a round-bar shaped test object 6 and probe module 12, the distance between the plurality of eddy current elements and the surface 42 of the test object 6 varies due to the curvature of surface 42. Notably, the lift-off (Lift-off A) associated with eddy current array element 2A is significantly less than the lift-off (Lift-off B) for eddy current array element 2B. This implies that the same defect on surface 42 could generate a stronger signal when located under array element 2A than when located array element 2B.

The lift-off distribution over the plurality of eddy current array elements 2 for module 12 is dependant on the diameter of test object 6 and the configuration of the EC inspection system. Given the diameter of the test object and the geometric configuration and diameter of the probe modules, the theoretical lift-off distance between each of the eddy current array elements 2 can be calculated using well practiced methods. It is known to those skilled in the art that the amplitude detected for a given defect is a function of lift-off and that this relation is substantially exponential. A factor for gain compensation in decibels required for a given eddy current array element as a function of the variation in lift-off compared to the gain required for the same eddy current element as determined on a calibration object can be calculated. This factor is typically in decibels per millimeter. The method of calculating lift-off gain compensation is described in details in *National Standard of Canada*: "Advanced Manual for Eddy Current Test, CAN/CGSB-48.14-M86".

Following the calculation of the lift-off variation for each element, a positive or negative gain can be applied to each element of the inspection system as a function of the lift-off variation from the calibrated lift-off associated to the element. For a given element, if the lift-off on the test object is greater than on the calibration object, the individual gain for the element in question will be increased by a factor in decibels per the difference in lift-off. For a given element, if the lift-off on the test object is less than on the calibration object, the individual gain for the element in question will be decreased by the same factor in decibels per millimeter. This compensation is performed individually for each of eddy current array elements.

Continuing with FIG. 4 in connection with FIG. 1-3, it must be noted that due to slight variations of the position of test object with respect to the axial center of the EC assembly 30, the spring tension compensation means as shown in FIG. 2 ensures uniform lift-off. As shown in FIG. 2, wear plate 24 is affixed to probe module 12a and employed to provide contact with test object 6. The elements in eddy current array 2 are offset from the contact surface of wear plate 24 so as to provide appropriate lift-off between eddy current array elements 2 and the surface of test object 6 when wear plate 24 is in contact with said surface of test object 6.

Various existing methods of treating lift-off can be adopted by the preferred embodiment of the invention described herein. Factory settings are typically included with a given inspection system. These factory settings typically include gain versus lift-off curves which are characteristic of the coils used in a system and the properties of the test object material such as whether this material is ferromagnetic or not. Further factory provided settings typically include the lift-off for each element as a function of the diameter of the test object being inspected. This relationship between lift-off and the test object diameter for each element can be provided in the form of graphs or equations. Calibration on a given calibration object provides the gain and impedance plane rotation required to equalize the signal on a calibration defect for each and every eddy current element in the system, wherein the calibration defect typically being a uniform notch around the entire circumference of the calibration object. Once calibration is performed on a known diameter calibration object, the gain compensation for each element in relationship with lift-off variations induced by the difference in circumference sizes between the calibration object and the test object can be derived from the lift-off versus diameter and gain versus lift-off information provided by the factory. Being different than these typical calibration procedures, the EC system with the preferred embodiment employed allows for calibration on any diameter of test object without changing probe heads, although it is recognized that the maximum diameter for a given inspection system is most advantageous.

Figure 5:
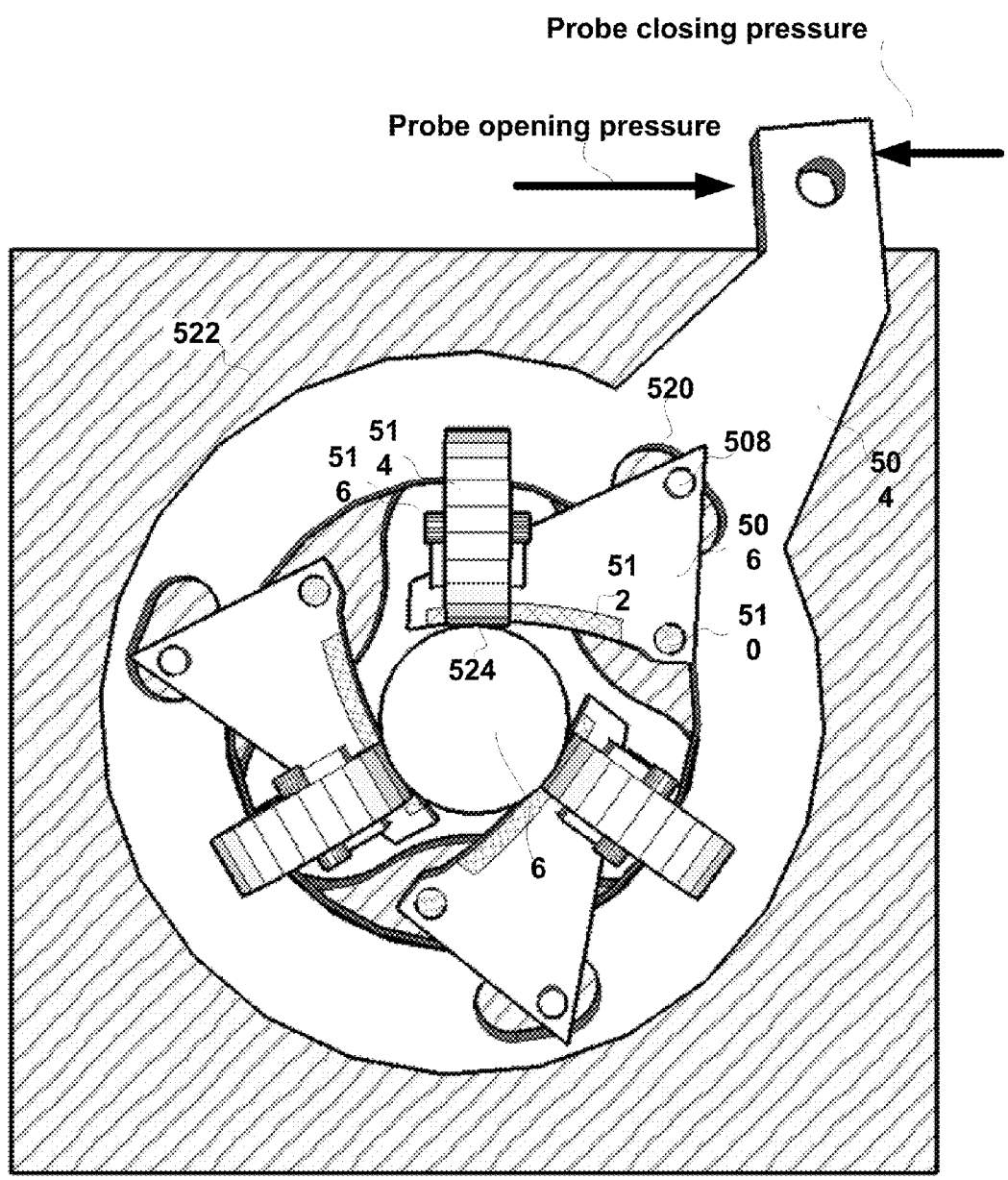
FIG. 5 is a cross-section view showing a probe head as depicted by an alternative embodiment of the present invention with guide wheels integrated with perspective probe modules

Detailed Description Of Alternative Embodiment I: Probe Assembly With Integrated Guide Wheels It should be noted that within the scope of the present disclosure, alternative embodiments can be employed. Notably, referring to FIG. 5, one of the alternative embodiments is shown.

In this alternative embodiment, instead of being separate from the guide wheels like in the preferred embodiment, probe modules, such as 506, are solidly affixed to a pair of guide wheels 514 and 516. Note that less than two and more than two guide wheels can be used and still remain within the scope of the current invention. Probe module 506 and guide wheels 514 and 516 are "opened" by applying probe opening pressure to rotation support plate 504 by rotating probe module 506 clockwise around rotation pivot point 510. For this alternative embodiment, probe module 506 can also be "closed" by directly applying probe closing pressure to rotation support plate 504 by rotating probe module 506 counterclockwise around pivot point 510.

It must be noted that alternate means can readily be appreciated for closing the probe module. Notably, a force opposite to probe opening pressure on rotation support plate 504 can be applied.

In the alternate embodiment described herein, the pair of guide wheels 514 and 516 come into contact with round test object 6. Eddy current elements 512 of probe module 506 are slightly recessed radially from the guide wheel contact point so as to provide appropriate lift-off of eddy current elements 512 with the surface of the test object 6.

Note that the alternative embodiment described herein employs three probe modules 506, each including their respective guide wheels 514 and 516 for each probe head 522 to provide equilibrated support for guiding round test object 6 through the inspection system. As with the preferred embodiment described previously, multiple probe heads are preferably disposed back-to-back longitudinally. In order to improve circumferential inspection coverage, each probe head is radially disposed in a way such that the probe modules from adjacent probe heads cover complementary sections of the surface of the test object.

Note that the profile of the guide wheels 514 and 516 is preferably made to match the profile of the surface of the inspection modules. This is a preferred but not a mandatory approach.

Operation: Calibration of the Disclosed Embodiments for Round Test Objects

Figure 6:
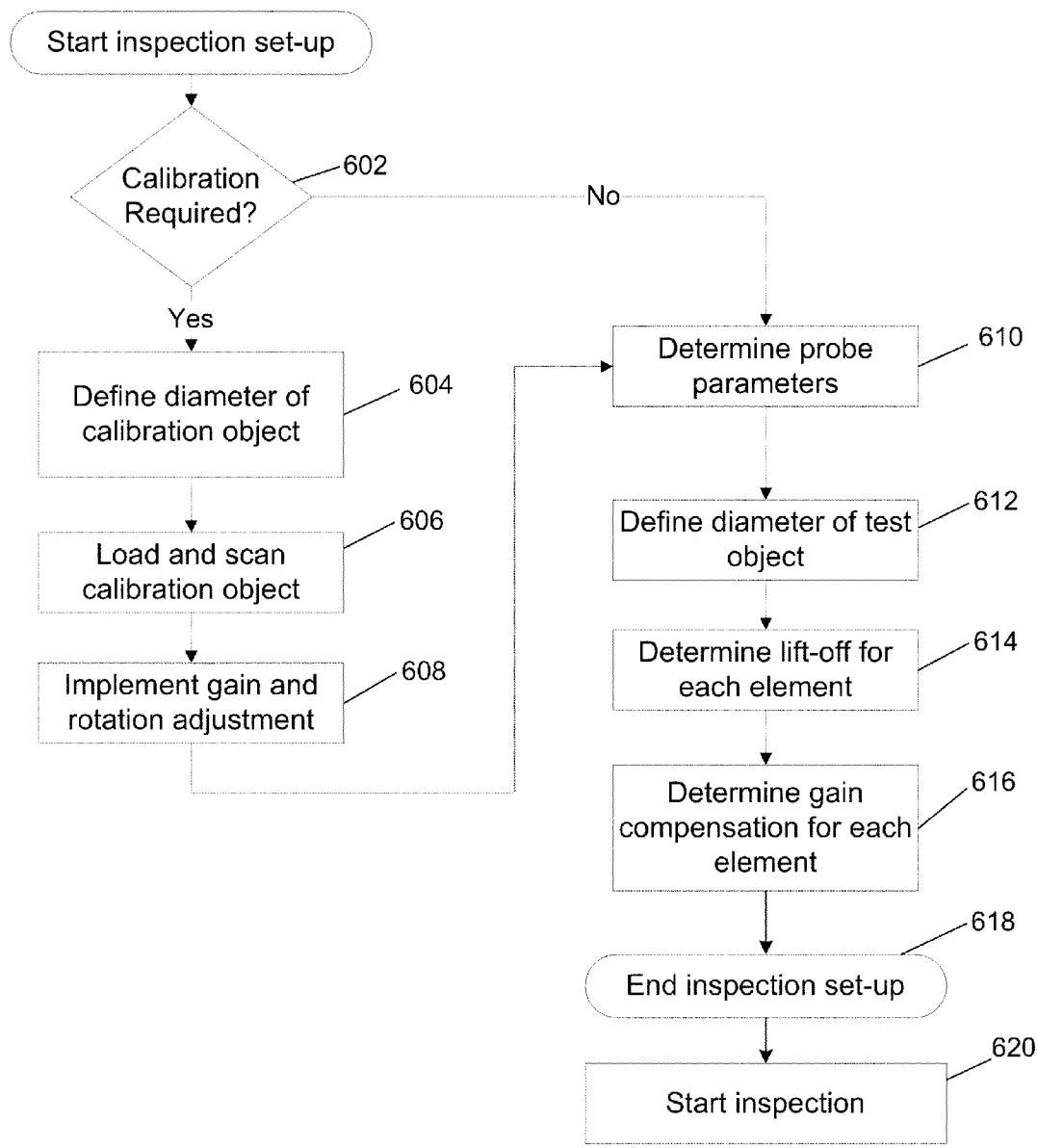
FIG. 6 is a flow chart describing an inspection set-up procedure for inspecting of cylindrical stock using presently disclosed ECA probe assembly.

An inspection set-up process for an EC inspection system with the presently disclosed probe assembly for inspecting round-bar or round-tube shaped test objects is shown in FIG. 6. As conventionally practiced in EC operations, a calibration procedure is typically only required when the material of the test object has changed or when other factors affecting the individual elements or probe module alignment have occurred. Calibration is performed for existing eddy current array inspection systems and aims to compensate for electronic variations between eddy current elements. Additionally, calibration of the inspection system described herein provides a means to also compensate for mechanical tolerances in the inspection system.

Referring to FIG. 6, an operator decides whether or not calibration is required in initial step 602. For situations where calibration is required, the calibration object diameter must be defined at step 604. Defining the calibration object diameter can be performed manually by the operator or determined automatically by other conventionally practiced means. The largest diameter calibration object provides the most uniform lift-off distribution for the greatest amount of eddy current array elements. The calibration object is fed through the EC inspection system at step 606. At step 608, the gain and impedance rotation are adjusted to equalize the signal of the calibration defect for each and every element in the inspection system. A uniform defect used for calibration can be, but is not limited to, a notch with uniform depth and width, completely encircling the calibration object circumferentially. Gain compensation can be performed manually but is usually an automated feature incorporated into typical inspection system software.

After the calibration procedure, or if the operator decides no calibration is required, the inspection system is readied to inspect bar or tube shaped test objects. At step 610, probe parameters are given by the operator based on the configuration of the presently invented probe heads and probe modules. The diameter of test object is provided to the inspection system 612. This can be achieved manually by the operator or automatically by the inspection system. It must be recognized that other means of providing test object diameter to the inspection system are possible.

With the above mentioned parameters determined in steps 610 and 612, the nominal lift-off for each element of the inspection system associated with the inspection of a given test object diameter can be determined in step 614.

At step 616, according to method described in aforementioned "Lift-Off Compensation" gain compensation is determined for each element by comparing the lift-off determined for each element of the EC system with the lift-off associated to the calibration object.

At step 618, the set-up is complete and the appropriate test objects with defined diameter can be inspected at step 620.

Advantageously, the invention described herein allows for calibrating on a given calibration object diameter and using the calibration parameters to inspect multiple round bar or round tube shaped test objects with the same or different diameter.

As can be noted by the skilled in the art that the elements are typically not in direct contact with the surface of the test object. Therefore, there exists a minimum lift-off for round test objects.

Detailed Description Of Alternate Embodiment Ii: For Polygonal Test Objects

The description and design of this alternative embodiment should be understood in corresponding way with those of the preferred embodiment.

Figure 7A:
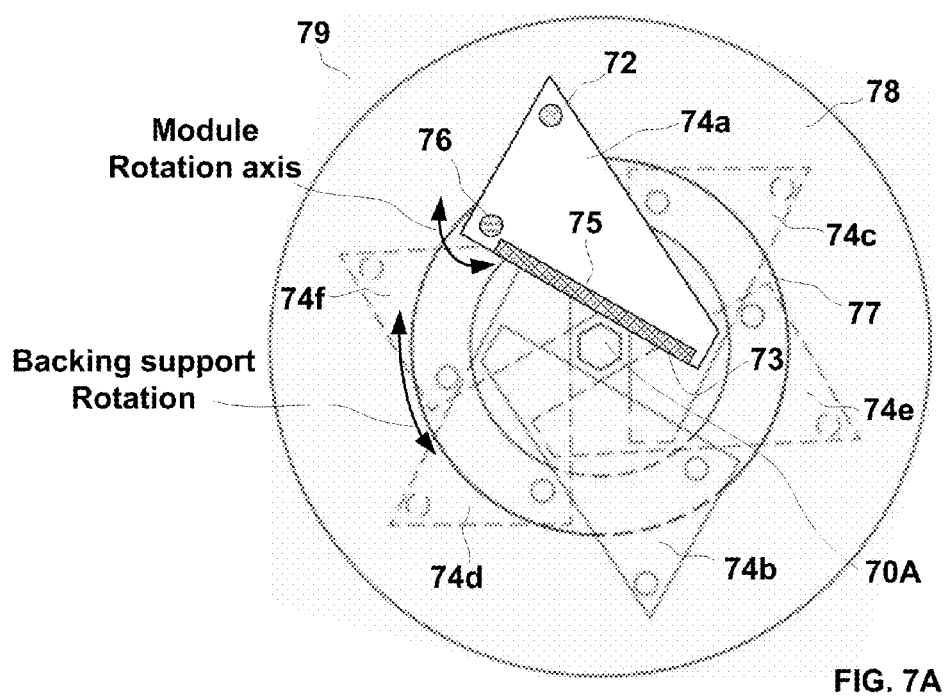
FIG. 7A and FIG. 7B are cross-sectional views showing an alternative embodiment of the present disclosure where the invented ECA probe assembly is configured to inspect two stocks polygonal rods of smaller and larger sizes, respectively.
Figure 7B:
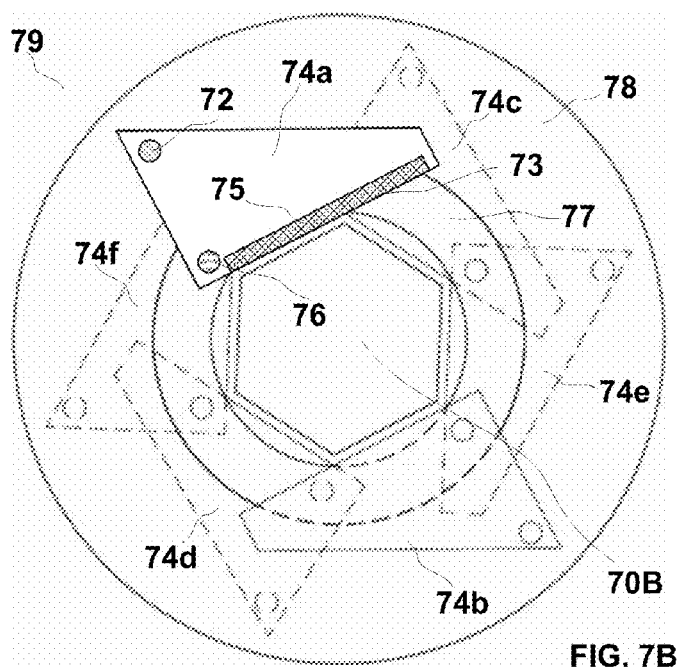

Referring now to FIG. 7A and 7B, alternative EC probe assemblies analogous to the preferred embodiment are shown for inspecting hexagonal test objects of smaller and larger sizes, respectively. Similar to the preferred embodiment, the assembly described herein comprises a plurality of probe modules 74a to 74f surrounding hexagonal test objects 70A and 70B. It must be noted that although the example describes a system for inspecting hexagonal test object, the invention is not limited in this respect. Any polygonal cross-section test object can be inspected within the scope of this invention.

Preferably in the EC assembly herein disclosed for inspecting hexagonal test objects, there are six probe modules disposed in three pairs, with each pair in the same radial plane. Probe modules 74*a* and 74*b* are grouped in the same radial plane. Additional pairs of probe modules can be grouped on planes offset along the longitudinal direction of the test object. For example, probe modules 74*c* and 74*d* are disposed in another radial plane offset longitudinally from probe modules 74*a* and 74*b*. Additionally probe modules 74*e* and 74*f* are offset from the previous pairs of probe modules. Collectively, each probe module is disposed to cover one surface of the hexagonal test object.

Using probe module 74*a* as an example, each probe module comprises an array of eddy current elements 75 for which at least a portion of the elements are in close and uniform proximity with one corresponding outer surface of hexagonal test object 70A. Each probe module is attached to backing support 77 by a rotation pivot point 76. Each probe module includes a size adjustment pin 72. Forces exerted on adjustment pin 72 induce a rotation of probe module 74*a* around rotation pivot point 76. Specifically, in the direction of motion, a clockwise force exerted on diameter adjustment pin 72 will force the probe module 74*a* and its associated eddy current array 75 away from the surface of small round test object 70A. Conversely, a counterclockwise force exerted on diameter adjustment pin 72 will force the probe module 74*a* to pivot towards the center of the inspection zone, thereby forcing the eddy current array 75 into proximity with hexagonal test object 70A.

A grouping of a given quantity of probe modules in the same axial plane as well as backing support 77 and rotation support plate 78 constitutes probe head 79.

The surface 73 of the eddy current array 75 on probe module 74*a* is shaped advantageously to maximize the proximity between the array 75 and the surface of the test object for a hexagonal test object. In this case, the surface of eddy current array 75 is flat.

In this alternate embodiment, backing support 77 is rotatable to provide rotary movement of pivot point 76 and other pivot points associated to other probe modules. This backing support rotary movement combined with the rotary movement for each probe module provides adaptability of the inspection system for a range of polygonal test object sizes. The backing support rotary position of 77, including the position of point 76 and pin 72 would be fixed for a given test object size once the test object is loaded.

To adjust the assembly to accommodate test objects with different sizes, backing support 77 is rotated clock or counterclock-wise and the probe modules are also opened or closed by forces exerted on pin 72.

As opposed to the preferred embodiment for round test object, an inspection system for hexagonal test object does not require lift-off compensation. The flat surfaces of the probe modules onto which the eddy current elements are disposed naturally match the substantially flat surface of each face of the hexagonal test object.

The EC assembly described herein can adapt to a plurality of test objects of beam or rod with different radially polygonal shapes and sizes. Adaptability for different test object shapes including round, hexagonal and square would potentially require changing the quantity of probe modules in a given probe head as well as the rotation support plates and backing supports to accommodate for the change in the number of probe modules. Specifically, hexagonal inspection systems would preferably use two or three probe modules per probe head, whereas square inspection systems would use two or four probe modules per probe head. The angular position of the probe module pivot points in a probe head would also be different to adopt the different angles provided by different polygonal cross sections. It must be noted however that the probe modules for hexagonal and square inspection systems can be but do not need to be the same.

Advantageously, the inspection system herein described uses a modular approach in which each probe head 79 preferably includes multiple probe modules 74 specifically configured to fit for certain shapes of test objects. The rotation support plate 78 and the backing support 77 can be swapped with another probe head to make the inspection system adapt to different shape test objects. This adaptability allows for inspecting variously shaped test objects on the same inspection line.

Inspection setup procedure for EC system using the probe assembly described in this polygonal embodiment is the same as that of conventional EC systems.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. An eddy current probe assembly configured to perform an inspection on a test object with longitudinal shape, being passed through the assembly in the object's axial direction during an inspection session, the probe assembly comprising a first plurality of probe modules being disposed in a first radial plane and with the modules arranged circumferentially relative to each other and forming an iris structure encircling an inspection zone, wherein a movement of each of the probe modules closer to or further away from the center of the inspection zone makes the inspection zone enlarged or contracted; wherein each probe module comprises a plurality of eddy current sensing elements which are disposed at a corresponding sensing surface of each of the first plurality of probe modules facing the inspection zone; wherein the sensing surfaces of all of the probe modules collectively substantially cover the entire circumference of the test object, wherein a second plurality of the probe modules is disposed in a second radial plane substantially next to the first radial plane, and each of the second plurality of the probe modules comprising a plurality of eddy current sensing elements disposed substantially at a sensing surface of each of the second plurality of probe modules facing the inspection zone, and, the sensing surface of the second plurality of probe modules is offset circumferentially from the sensing surface of the first plurality of probe modules so that the circumference of the test object is sufficiently covered by the sensing surfaces.

2. The probe assembly of claim 1, in which the assembly is in a closed position during the inspection session wherein each of the probe modules is located closer to the center of the inspection zone and the sensing surface is substantially contiguous with the outer surface of the test object.

3. The probe assembly of claim 1, the assembly further comprising at least one diameter fixing means for stopping the movement of each of the probe modules from moving further closer to the test object so that the sensing surface of the probe modules is very close to but not contiguous with the outer surface of the test object.

4. The probe assembly of claim 1, in which the assembly is in an open position during a test object loading session wherein each of the probe modules is located away from the center of the inspection zone.

5. The probe assembly of claim 1, in which the radial cross-sectional size of the test object is smaller or larger when the inspection zone is enlarged or contracted, respectively.

6. The probe assembly of claim 5, the assembly comprising a backing support element on which there is a groove element for each respective probe module, and each of the probe module further comprising an inspection size adjustment pin slidable substantially inside the groove element, wherein the sliding movement causes the probe module to rotate around the rotation pin and subsequently causing the probe module to move towards or away from the center of the inspection zone.

7. The probe assembly of claim 6, in which the spring tensions for all the probe modules are substantially equal so that a substantially constant proximity is maintained between the circumferrencial surface of the test object and all of the probe modules.

8. The probe assembly of claim 1, each of the probe modules comprising a rotation pin which is installed substantially away from the center of the inspection, the movement of each probe module being rotational around the rotation pin.

9. The probe assembly of claim 8, the assembly comprising a spring element for each of the probe modules connecting the respective rotation pin and the backing support element so that a spring tension is exerted on each of probe modules, and subsequentially each of the probe modules leans substantially against the test object.

10. The probe assembly of claim 8, in which all the probe modules can be rotated away from the center of the inspection zone when an opening pressure is applied to the backing support element.

11. The probe assembly of claim 1, the assembly further comprising a plurality of guide wheels installed in an arrangement selected from a group consisting of before, after and before and after the first plurality of probe modules to center the test object passing through the probe modules axially.

12. The probe assembly of claim 11, in which the backing support element and the guide wheels are installed on a support structure.

13. The probe assembly of claim 1, the assembly comprising a plurality of guide wheels installed in an arrangement selected from a group consisting of before, in between, after and before and after and before and in-between and after the first and the second plurality of probe modules to center the test object passing through the probe modules axially.

14. The probe assembly of claim 1, each of the probe modules further comprising at least one guide wheel attached to the respective probe module wherein the guide wheel centers the test object passing through the probe modules axially.

15. The probe assembly of claim 14, wherein an operation setup procedure is applied to an inspection system employing the probe assembly, the setup procedure further comprising a step allowing the radial diameter of the test object to be adjusted after a calibration procedure for lift-off compensation is performed on the inspection system.

16. The probe assembly of claim 1, in which the radially cross-sectional shape of the test object is round.

17. The probe assembly of claim 1, in which the radially cross-sectional shape of the test object is polygonal.

18. The non-destructive inspection probe assembly in claim 1, wherein the assembly is configured to perform the inspection with axial movement of the test object.

* * * * *